United States Patent [19]
Nordquist et al.

[11] Patent Number: 6,099,554
[45] Date of Patent: *Aug. 8, 2000

[54] LASER LIGHT DELIVERY METHOD

[75] Inventors: Robert E. Nordquist, Oklahoma City; Wei R. Chen, Edmond, both of Okla.

[73] Assignee: Wound Healing of Oklahoma, Oklahoma City, Okla.

[*] Notice: This patent issued on a continued prosecution application filed under 37 CFR 1.53(d), and is subject to the twenty year patent term provisions of 35 U.S.C. 154(a)(2).

[21] Appl. No.: 09/053,323

[22] Filed: Apr. 1, 1998

Related U.S. Application Data

[60] Provisional application No. 60/040,899, Apr. 2, 1997.

[51] Int. Cl.[7] .................................................. A61N 5/00
[52] U.S. Cl. ............................ 607/89; 607/91; 606/13; 606/17
[58] Field of Search ............................. 607/88, 89, 91, 607/92, 93; 606/2, 9, 13.17; 250/453.11, 454.11, 493.1, 494.1; 604/19.2

[56] References Cited

U.S. PATENT DOCUMENTS

| | | | |
|---|---|---|---|
| 4,619,249 | 10/1986 | Landry | 607/93 |
| 5,150,704 | 9/1992 | Tatebayashi et al. | 606/10 |
| 5,259,380 | 11/1993 | Mendes et al. | 606/2 |
| 5,445,608 | 8/1995 | Chen et al. | 607/89 |
| 5,470,331 | 11/1995 | Daikuzono | 606/13 |
| 5,489,279 | 2/1996 | Meserol | 607/89 |
| 5,549,660 | 8/1996 | Mendes et al. | 607/88 |
| 5,800,478 | 9/1998 | Chen et al. | 607/92 |
| 5,807,387 | 9/1998 | Druais . | |

FOREIGN PATENT DOCUMENTS

| | | |
|---|---|---|
| 0 320 080 | 6/1989 | European Pat. Off. . |
| 0 464 207 | 1/1992 | European Pat. Off. . |
| WO 90 00420 | 1/1990 | WIPO . |
| WO 97 45163 | 12/1997 | WIPO . |

OTHER PUBLICATIONS

Database Inspec, Institute of Electrical Engineers, Stevenage, GB. Inspc No. 0003–6935, Nov. 1, 1997. Wang, Nordquist, Chen: "Optimal beam size for light delivery to absorption–enhanced tumors buried in biological tissues and effects of multiple–beam delivery: a Monte–Carlo study." XP002069527. See abstract.

Wang, Norquist, Chen: "Optical beam size for light delivery to absorption–enhanced." Applied Optics, vol. 36, No. 1, Nov. 1, 1997, USA, pp. 8286–8291, see the whole document.

*Primary Examiner*—Linda C. M. Dvorak
*Assistant Examiner*—Bryan K. Yarnell
*Attorney, Agent, or Firm*—Fellers, Snider, Blankenship, Bailey & Tippens, P.C.

[57] ABSTRACT

A method for the delivery of laser light for therapeutic purposes, and, more specifically, for the treatment of buried tumors wherein multiple lasers are used to treat a deeply buried tumorous mass. In more particular, multiple lasers in a spatial array are used to simultaneous irradiate a tumor from a multiplicity of different directions. Tumors treated in this way are heated more homogeneously than those treated via conventional single-laser treatments. Additionally, a multiple source laser treatment scheme puts the enclosing normal tissue at lesser risk than it would be exposed to if the treatment were conducted using via a single laser source.

9 Claims, 3 Drawing Sheets

LASER LIGHT DELIVERY METHOD

This application claims the benefit of U.S. Provisional Application No. 60/040,899, which application was filed with the Patent and Trademark Office on Apr. 2, 1997.

BACKGROUND OF THE INVENTION

1. Technical Field

This invention relates generally to systems and methods for the delivery of laser light for therapeutic purposes, and, more specifically, to laser light delivery systems for the treatment of buried tumors.

2. Background

Laser/tissue interactions and therapeutic applications of laser light are two rapidly growing areas of research. As is well known to those skilled in the art, high intensity laser beams have the potential to destroy bodily tissue, a property that can be turned to usefull purposes in the field of tumor treatment, where the term "tumor" will be used hereinafter to describe any cellular mass that serves no physiological function including cancers, neoplasms, neoplastic masses, etc. The growth of a tumorous mass can be retarded or even stopped through the application of thermal energy, and a laser provides a precise, concentrated, and highly controllable means of delivering that energy. Tumors on the surface of the body—and those that can be made visible through surgery or other means—are excellent candidates for such treatment and often respond favorably to the direct application of laser light. However, tumors that are buried deep within healthy tissue pose a special problem for laser methods. In more particular, since lasers are ultimately just coherent light sources, any attempt to "illuminate" a buried tumor with laser light must necessarily also illuminate the tissue that lies between the laser source at the surface and the tumor. Thus, the heat from a laser that is directed at a buried target has the potential to destroy, not only the tumor, but also the tissue that encloses it.

Basic physics provides an explanation of why this should be so. Biological tissues are turbid media and light that passes therethrough is continually absorbed by the conducting tissue during its passage. Additionally, bodily tissue is a strong light scatterer and additional energy is lost from the beam during its transmission due to this effect. The absorbed and scattered radiant energy is converted into thermal energy (heat), which energy has the potential to damage the tissue within and along a laser beam's path. These two effects can combine to substantially reduce the potential effectiveness of laser treatment of buried tissues because each unit of radiant energy that is lost during the beam's transmission to the tumor represents one less unit of energy that can be applied to heat its ultimate target. Thus, one of the principal obstacles to the use of laser light to treat a buried tumor is that the tumor may potentially receive much less optical power than the surrounding subsurface healthy tissues.

Broadly speaking, there are three general approaches to overcoming the aforementioned obstacle, the ultimate goal being to maximize the power delivered to the target tumor while minimizing the risk of collateral damage to other tissues. First are dye-based treatments which aim to increase the light absorption coefficient of the tumor by infusing it with one or more special dyes. This makes possible the use of a lower power laser light source, as the dye-infused tumor will tend to heat more rapidly than the surrounding tissue. Another approach involves manipulation of the wavelength of the laser light and the selection of a wavelength to which the tumor is more responsive than is the surrounding normal tissue. Finally, a third broad approach involves selection of a light delivery scheme which maximizes the power absorption by the target tumor and minimizes the exposure of the surrounding tissue to thermal stress. The present invention is directed to this last approach.

Thus, what is needed is a laser delivery system that can efficiently convey a maximum amount of optical power to a buried tumor while reducing the risk of collateral damage to the surrounding normal tissue. Additionally, it should also be designed so that the laser light is selectively applied to tumorous tissue rather than normal tissue. Finally, the lasers that comprise the system should be sized such that they maximize the power coupling efficiency and the power delivered to the buried tumor.

Accordingly, it should now be recognized, as was recognized by the present inventors, that there exists, and has existed for some time, a very real need for a laser light delivery system that would address and solve the above-described problems.

However, before proceeding to a description of the present invention it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

The present invention relates generally to an apparatus and method for achieving improved optical power deposition into a tumor tissue mass. In theoretical terms, the invention described herein is founded broadly on the observation that whenever laser light is used to heat a deeply buried tumor, waste heat is generated as the light travels to the tumor through the enclosing tissue. If only a single laser light source is used, as is the practice in the prior art, all of the waste heat is released along a single path. However, the instant inventors have discovered that if an array of multiple laser sources is used, it is possible to deliver the same optical power to the tumor while spreading the inevitable waste heat along multiple paths. This reduces the maximum exposure of any particular volume of healthy tissue to the laser's effects, which correspondingly reduces the risk of collateral damage. Additionally, the instant inventors have discovered that irradiation of a tumor by an array of lasers carries with it another benefit in that the tumor may be heated more homogeneously.

In accordance with one aspect of the instant invention, there is provided a laser light delivery system which utilizes multiple laser beams to simultaneously irradiate a tumor mass from a variety of different directions. In the preferred embodiment, a plurality of optical fibers, through which laser light is conducted, are held in a circumferential spaced-apart relationship surrounding a buried tumor. The respective termini of the optical fibers are aimed generally toward the target tumor and, when the unit is in operation, the tumor is irradiated on all sides by laser light emanating from the optical fibers. Preferably the optical fibers are provided in pairs, with each pair member being on an opposite side of the target tumor and each member of the pair being directed toward the other. Additionally, it is preferred that the exit ends of the optical fibers lie in a single horizontal plane, although many other spatial arrangements are certainly possible and have been specifically contemplated by the instant inventors. Finally, it is preferred, though not required, that the laser light sources be activated simultaneously.

Each optical fiber is preferably held in place by an arm of a light delivery apparatus, which arm is connected to the arm holding the oppositely disposed fiber by a tension or pull spring. Thus, the pairs of opposed arms act much like a caliper with each arm holding an optical fiber in a common plane. The pairs of arms are supported by a housing consisting of two axially aligned slotted stages.

The radius of each of the optical fibers—and, hence, the radius of the emitted laser beam—is preferably determined by reference to a specific equation which relates an optimal radius to the particular optical parameters of the lased tissue. Using the preferred optical fiber radii results in a laser light treatment that is more homogeneous and provides a more intense power deposition into the tumor mass than is possible if only a single laser is used.

Finally, the invention disclosed herein might be useful in any number of medical treatment scenarios where lasers are currently used or might potentially be used including photothernal therapies, photomechanical therapies, and noninvasive photosensitizer-assisted laser therapies of deep tumors.

The foregoing has outlined in broad terms the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

DETAILED DESCRIPTION OF THE PREFERRED EMBODIMENT

Figure 1:
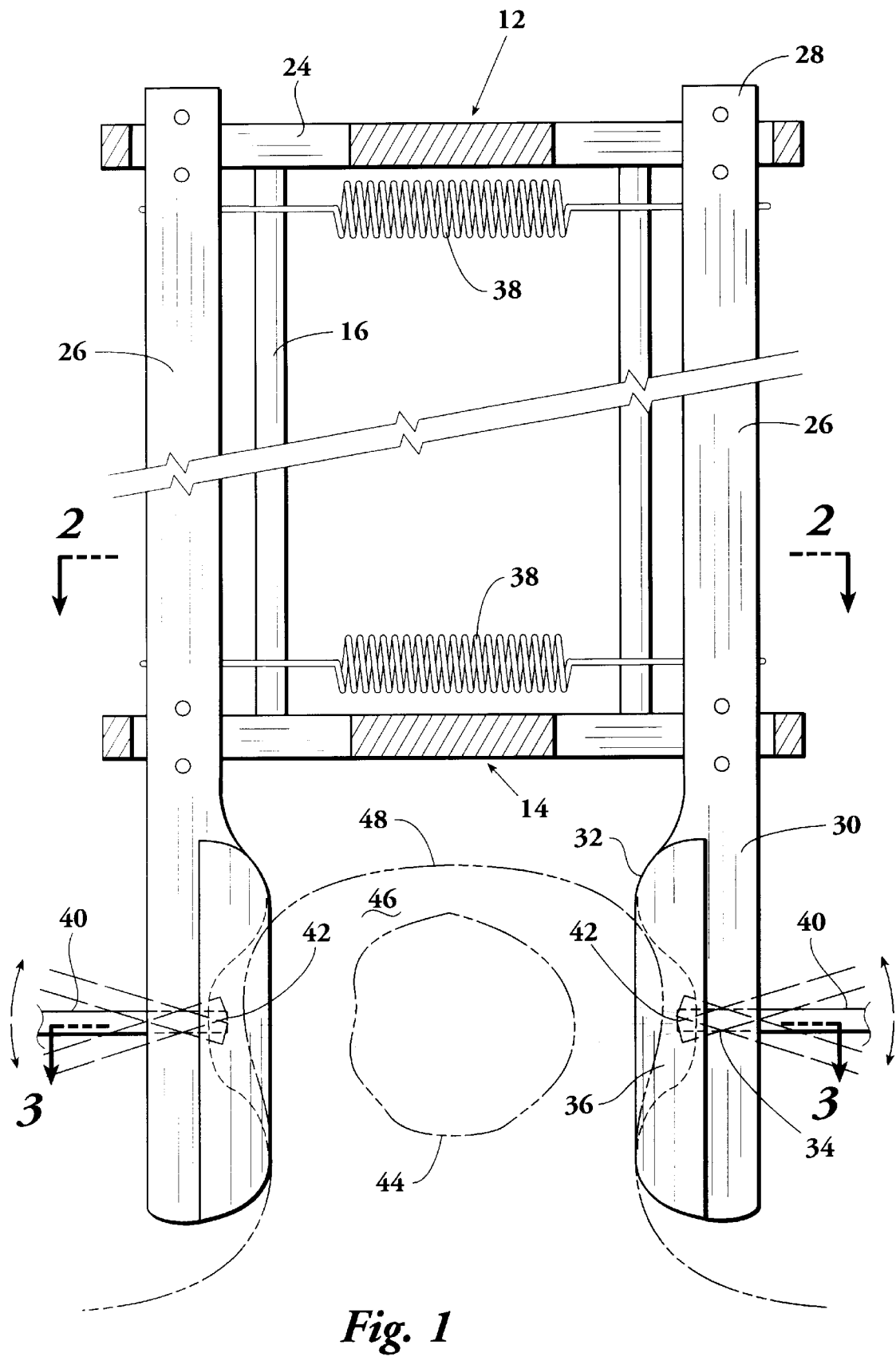
FIG. 1 is an elevational view showing one embodiment of the instant invention wherein one pair of opposing arms with oppositely disposed optical fibers are arranged on either side of a buried tumor mass.
Figure 4:
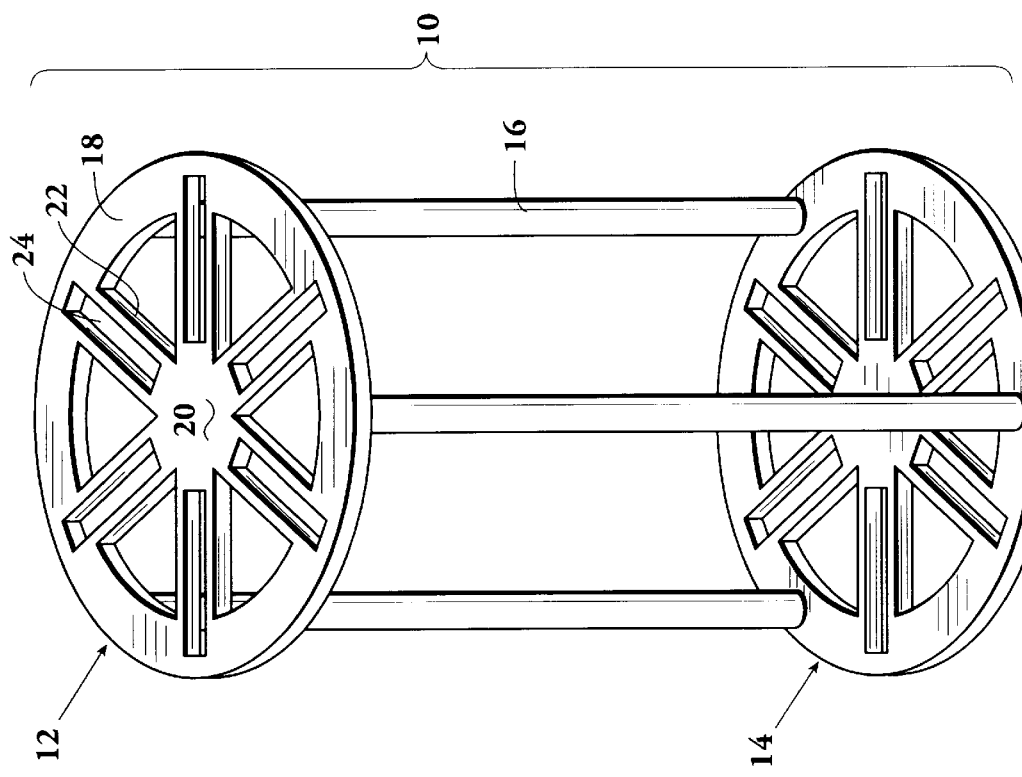
FIG. 4 is an isometric view of the light delivery system housing.

The present invention provides a new apparatus and method for the irradiation of tumors wherein multiple laser light sources are used. Referring first to FIGS. 1 and 4, wherein a preferred embodiment of a light delivery system for multiple beam delivery is illustrated, the light delivery system includes a housing which is generally indicated by the reference numeral 10. The housing 10 preferably comprises an upper stage 12 and a lower stage 14 maintained in axial alignment by a number of connecting bars 16. Each stage consists of a circumferential ring 18 connected to a central hub area 20 by a number of spokes 22. Each of the spokes 22 contains a slot or longitudinal aperture 24. The upper stage 12 and lower stage 14 have a common longitudinal axis and the slots of the upper stage 12 are aligned with the slots of the lower stage 14.

Figure 5:
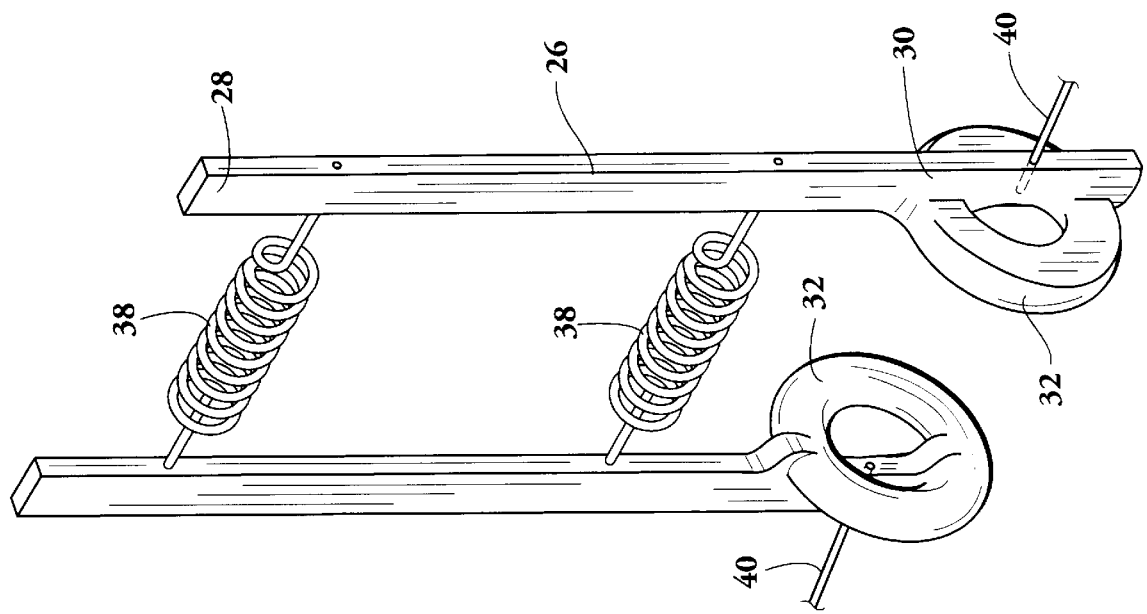
FIG. 5 is an isometric view of one pair of opposing arms urged inwardly by tension springs.

Resident within each corresponding pair of slots 24 is an optical fiber support arm 26. Referring now to FIGS. 1 and 5, each arm 26 has an upper end 28 extending through the slot 24 in the upper stage 12 and a lower end 30 extending through the corresponding slot in the lower stage 14. The lower end 30 of the arm 26 is preferably provided with an annular ring 32 at its terminus, the annular ring 32 functioning as a contacting surface for placement against the area to be treated. A bore 34 extends transversely through the lower end 30 of the arm 26 at a point corresponding to the center of the annular ring 32. The lower end 30 of the arm 26 is contoured in a U-shape such that a space 36 is created between the surface of the annular ring 32 and the bore 34.

Figure 2:
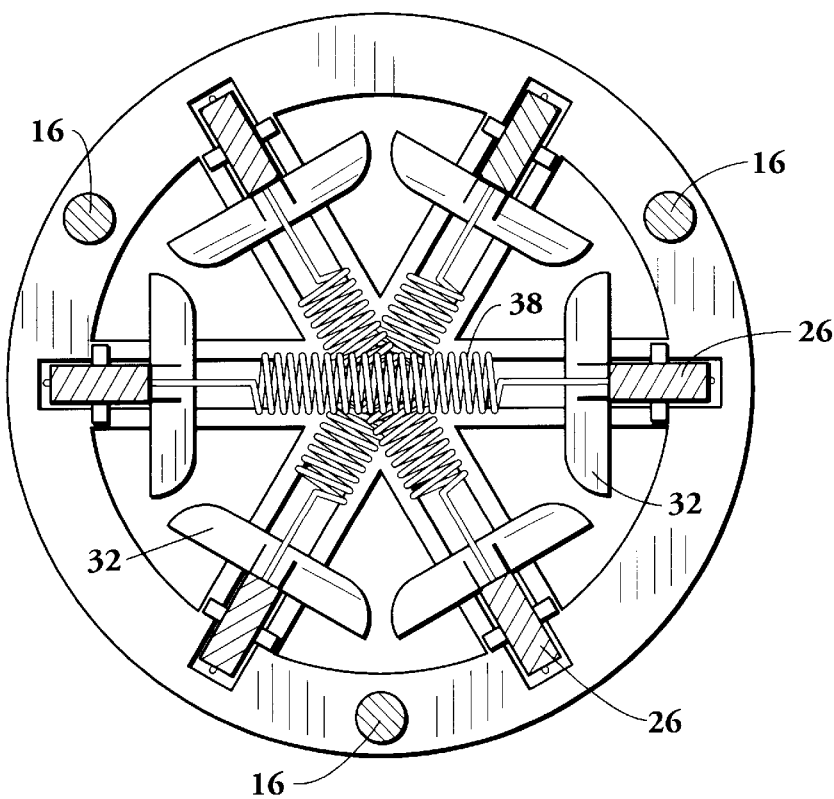
FIG. 2 is a view taken along cutting plane 2—2 of FIG. 1. This view shows three pairs of opposing arms. The springs are in different horizontal planes so as not to interfere with each other.

In the preferred embodiment, a pair of tension or pull springs 38 urge each pair of opposing arms 26 inwardly. One tension spring 38 is positioned below the upper stage 12, while another is positioned slightly above the lower stage 14. One or more tension springs 38 or similar devices may be used to provide an inwardly directed force to each pair of opposing arms. As shown in FIG. 2, the tension springs 38 lie in different horizontal planes so as not to interfere with each other. Additionally, those skilled in the art will recognize that any number of other devices and materials might be used in place of conventional metal springs to urge the opposing arms 26 together including—but not limited to—rubber straps, elastic bands, threaded nut and bolt combinations, etc. Thus, the term "tension spring" will be used hereinafter to refer generally to any device of this sort that tends to urge the two arms together.

An optical fiber 40 lies in the bore 34 of each arm 26, and the exit end 42 of each optical fiber 40 preferably protrudes slightly from the margin of the arm 26. The purpose of the optical fibers 40 is to conduct laser light from its source to the instant device where it is emitted from the exit ends 42. In the text that follows, "laser light source" will be taken to include not only the actual lasers, but also the exit end 42 and the optical fiber 40/exit end 42 combination as they are, for all practical purposes, laser light sources themselves.

The exit end 42 of the optical fiber 40 lies in the space 36 created by the annular ring 32 of the U-shaped lower end 30 of the arm 26. The bore 34 is shown as being horizontal and the exit end 42 as being perpendicular to the longitudinal axis of the arm 26, however, it is within the scope of the present invention to angle the bore 34 or manipulate the emergence angle of the optical fiber 40—and particularly the orientation of the exit end 42 of the optical fiber—so that the energy from each laser may be aimed out of the plane formed by the exit ends 42. This arrangement makes it possible to adjust the irradiation angle so that some tumors that cannot be brought within the confines of the device can be treated. Additionally, although it is preferred that the lasers are generally aimed toward the same point in the tissue subsurface, it is anticipated that in some circumstances the orientation of each laser might be adjusted somewhat away from aiming at a single point so as to produce a more diffuse effect, thereby increasing the size of the treated region.

In its preferred use, the device delivers laser power to a buried tumor. Shown in phantom lines in FIG. 1 is a buried tumor 44 lying within subcutaneous tissue 46. In practice, the location of the tumor 44 is typically determined in advance by means such as ultrasonography, x-ray, and/or palpation. The absorption of the thermal energy from the laser by the tumor is preferably enhanced by infusing it with a photosensitizer, such as indocyanine green, prior to laser treatment by the instant invention.

Figure 3:
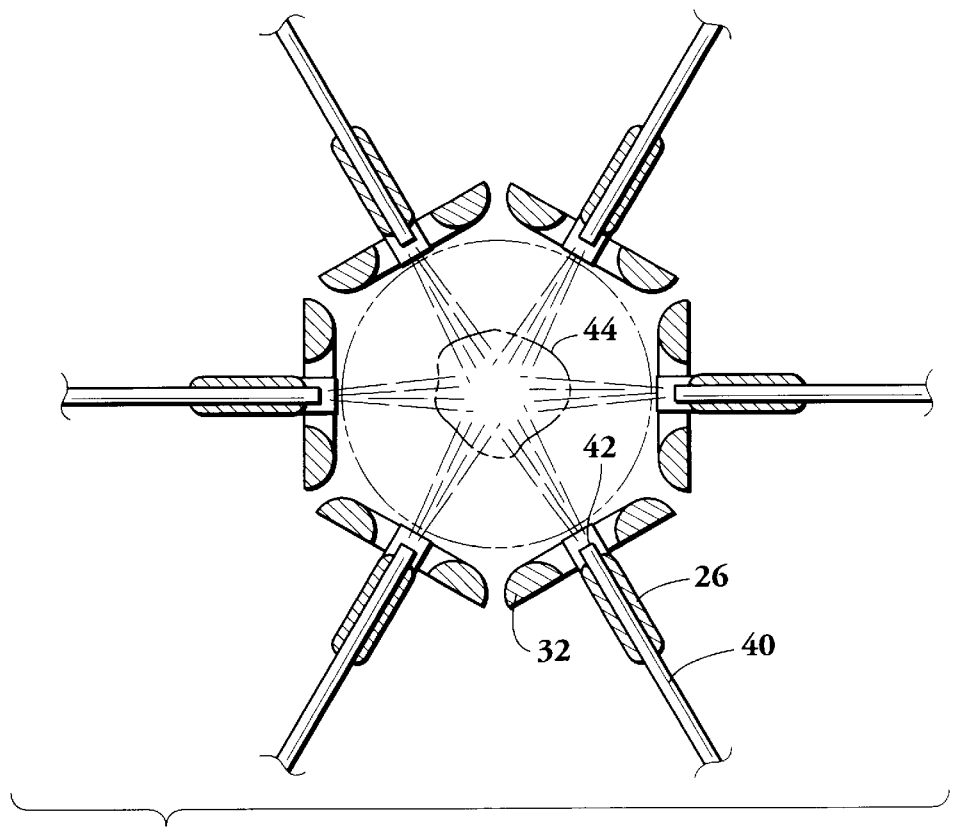
FIG. 3 is view taken along cutting plane 3—3 of FIG. 1. This figure shows three opposing pairs of optical fibers, held by opposing arms, pointing at the tumor mass.

In application, the arms 26 of the device are preferably positioned circumferentially about the tumor 44, with the exit ends 42 of the optical fibers 40 being aligned with the center of the tumor. A remote lasing apparatus or apparatuses (not shown) is then activated; its beams are guided into the remote ends (not shown) of the optical fibers 40; the laser light is carried through the optical fibers 40 to the instant device; and, the laser light is emitted from the exit ends 42 of each of the optical fibers 40. As illustrated in FIGS. 1 and 3, the tumor 44 is lased—preferably simultaneously—from a number of different directions to achieve a more homogeneous and intense power deposition in the tumor 44 than was previously available.

It is not essential that all of the optical fibers 40 emit laser light in every application. In fact, it has been specifically contemplated by the instant inventors that fewer laser light sources might be utilized depending on the circumstances. By way of example, it is possible that only two of the six lasers in FIG. 3 might actually be activated in a particular case, the remaining exit ends 42 of the optical fibers having been blocked. However, using more beams generally results in a more homogenous and intense power deposition into the tumor, and thus that would be the preferred embodiment. Additionally, although the exit ends 42 of the optical fibers 40 in FIG. 3 are arranged at equally spaced intervals about the perimeter of a circle, this is not essential to the operation of the invention. Indeed, it is preferred that the exit ends 42 be positioned so that, insofar as it is possible, a given volume of healthy tissue is exposed to waste heat from only one of the laser beams. That being said, it is anticipated that the exact number, positions, and orientations of the exit ends 42 may have to be customized depending, for example, on the location of the tumor within the body. In some cases, it may be impossible to "surround" or encircle the tumor with the laser array because of the tumor's location. In those cases, the lasers could instead be arranged into a semi-circular or some other array pattern. Whatever the spatial arrangement or pattern, however, it is critical that the active lasers all be aimed generally toward the same region of the body if the most favorable therapeutic results are to be obtained.

Preferably, the exit end 42 of each optical fiber 40 is positioned 1 mm to 2 cm away from the surface of the skin 48. The laser energy is then delivered to each optical fiber 40 from one or more laser sources. For purposes of the instant application, each optical fiber 40 will be spoken of as though it were powered by a separate laser, although that is not essential and, in fact, a single laser beam—properly divided—might act as a source for the entire array of optical fibers 40.

While it is preferred that the optical fibers 40 be configured in oppositely disposed pairs having their exit ends 42 in a common horizontal plane, it should be understood that the present invention also encompasses the use of a plurality of optical fibers 40 arranged into a spatial array of laser sources. The term "spatial array" will be understood herein to mean any two or three dimensional (3-D) arrangement of individual laser sources, wherein the lasers are aimed generally toward the same target. The spatial array might take a planar (two dimensional) form like the near-circular arrangement illustrated in FIG. 3, wherein the tumor is situated within the body of the device (i.e., within the spatial array) and is surrounded by the laser sources. More generally the spatial array might take a 3-D form wherein the laser sources are arranged, for example, on the surface of a dish or other concave object, the curvature of the disk being preferably chosen so as to help train the lasers sources on the target.

The component parts of the instant laser light delivery system may be machined from surgical steel or extruded or molded using a strong, preferably autoclavable, plastic in manners well known in the art.

The various parameters of the lasers are preferably selected as described hereinafter, taking into account the light absorptive capacity of the tumor and the optical properties of the tissue that surrounds it. It should be noted at the outset that when an array of lasers is used, it is possible to decrease the wattage (power) of each laser as compared with the power that would be typically required of a single laser. Within limits, the power of each individual laser source may be decreased by a factor roughly proportional to the number of lasers in the array. That is, when two lasers are used, each may be set to deliver approximately one-half of the wattage that would normally be required of a single laser. If the two laser array is correctly positioned (preferably with each on an opposite sides of the tumor) the therapeutic effect of the two lasers will typically exceed that of a single laser of the same total power which is applied from a single direction. Furthermore, in the case of treatments such as photothermal immunotherapy—where the objective is not the total destruction of the tumor—the source power can be reduced to an even more tolerable level.

The particular choice of the laser light wavelength is not critical to the instant invention, but in the preferred embodiment an 805 nm diode laser should be used if indocyanine green is employed as the photosensitizer. Other choices are certainly possible and those skilled in the art will understand the various considerations that go into making the choice of a laser wavelength.

Finally, the radius of the laser (as measured, for example, by the radius of the exit end 42) is preferably chosen according to the following equation:

$$r_o = [\delta(2d_t - 2L_t' + \delta)]^{1/2}$$

where $r_o$ is the preferred laser radius, $d_t$ is the distance between the center of the tumor and the upper tissue surface, $\delta$ is the penetration depth of the laser, and $L_t'$ is one transport mean free path. The variables $L_t'$ and $\delta$ are further defined in terms of the optical properties of the healthy (or "background") tissue:

$$L_t' = 1/[\mu_a + \mu_s(1-g)],$$

and $$\delta = \sqrt{3\mu_a[\mu_a + \mu_s(1-g)]},$$

where, $\mu_a$ is the absorption coefficient of the non-tumorous tissue, $\mu_s$ is its scattering coefficient, and g its anisotropy factor. Those skilled in the art will recognize that $\mu_a$ is generally defined to be the probability of photon absorption per unit infinitesimal path length within the transmitting tissue; $\mu_s$ is the probability of photon scattering per unit infinitesimal path length; and, g is the average of the cosine value of the deflection angle by single scattering.

By way of example, if the optical properties of the background tissue are $\mu_a = 0.1 \text{ cm}^{-1}$, $\mu_s = 100 \text{ cm}^{-1}$, $g = 0.9$, and the distance between the center of the tumor and the upper tissue surface $d_t$ is 1.5 cm, the transport mean free path can be calculated to be:

$$L_t' = 1/[\mu_a + \mu_s(1-g)] = 0.099 \text{ cm},$$

and the penetration depth is $$\delta = \sqrt{3\mu_a[\mu_a + \mu_s(1-g)]} = 0.57 \text{ cm},$$

resulting in an estimated radius $r_o$ of 1.39 cm. Note that, not only is this a preferred laser radius, but it also will be an optimal choice where the tissue parameters match those of the example.

Choosing the laser beam radius according to the preceding formulas can result in a more effective laser therapy for deep tumors. As a general rule, the broader the radius of the beams, the more homogeneous the power deposition in the tumor will be, with the preferred radius $r_o$ of the laser beams providing near optimal thermal deposition within the tumor. Through the use of the instant guideline for choosing $r_o$, practitioners can potentially avoid unnecessary exposure and heating of skin's surface (i.e., the beam radius is too large) and damage caused by a peak power deposition (a "hot spot") near the tissue surface (i.e., the beam radius is too small).

In summary, the instant inventors have discovered that an array of laser sources produces a more homogeneous and intense power deposition into a target tumor. The fact that the maximum power absorption by background tissue can be reduced with multiple beams to the level comparable to that absorbed by the tumor shows the promise for better therapeutic outcomes, especially where the laser array is used in conjunction with an optimized configuration of tumor dyes. Additionally, as is well know to those skilled in the art, surface cooling with liquid or gas can be used in conjunction with the instant invention to further drastically reduce the energy accumulation within the surface tissue. Scanning the laser beams during the treatment can also be employed to reduce surface heating and this feature could also be incorporated within the instant invention. Finally, although the preferred embodiment of the instant invention contains six laser light sources, it is specifically contemplated by the instant inventors that an increase in the number of beams beyond six could also be beneficial in some cases.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method for the treatment of a tumor by laser light, wherein is provided a patient having a tumor, comprising the steps of:
   (a) identifying at least an approximate location of the tumor within the patient;
   (b) obtaining at least three spaced-apart laser light sources, each of said laser light sources emitting a beam of laser light when activated;
   (c) orienting each of said at least three spaced-apart laser light sources so that a focused array is formed, wherein each of said at least three spaced-apart laser light sources is aimed generally toward a same point within the tumor and wherein each of said at least three spaced-apart laser light sources is situated externally to the patient's body; and,
   (d) activating said at least three spaced-apart laser light sources, thereby irradiating substantially said same point within the tumor with at least three convergent spaced-apart beams of laser light.

2. A method according to claim 1 wherein a photosensitive dye is infused into the tumor before the tumor is irradiated in step (d).

3. A method for the treatment of a tumor by laser light according to claim 2 wherein said photosensitive dye is indocyanine green.

4. A method for the treatment of a tumor by laser light according to claim 1, wherein each of said laser light sources of step (b) emits a beam of laser light at a wavelength of about 805 nm when activated.

5. A method for the treatment of a tumor by laser light according to claim 1, wherein step (d) includes the step of simultaneously activating each of said at least three spaced-apart laser light sources.

6. A method for the treatment of a tumor by laser light according to claim 1, wherein step (c) includes the step of orienting said at least three spaced-apart laser light sources so as to form a focused spatial array of spaced-apart laser light sources.

7. A method for the treatment of a tumor by laser light according to claim 6, wherein said focused spatial array of spaced-apart laser light sources is a focused planar array of spaced-apart laser light sources.

8. A method for the treatment of a tumor by laser light according to claim 7, wherein said planar array of spaced-apart laser light sources is a circular array of laser light sources.

9. A method for the treatment of a tumor by laser light according to claim 8, wherein said at least three spaced-apart laser light sources are arranged at equal intervals about a perimeter of a circle.

* * * * *